United States Patent [19]

Fiske et al.

[11] 4,147,733

[45] Apr. 3, 1979

[54] FLUORINATION OF CHLORINATED HYDROCARBONS

[75] Inventors: Tom R. Fiske; Daniel W. Baugh, Jr., both of Baton Rouge, La.

[73] Assignee: The Dow Chemical Company, Midland, Mich.

[21] Appl. No.: 908,310

[22] Filed: May 22, 1978

[51] Int. Cl.² ..................... C07C 17/08; C07C 17/15
[52] U.S. Cl. .............................. 260/653.4; 260/653.3; 260/653.7
[58] Field of Search ................ 260/653.3, 653.4, 653.7

[56] References Cited

U.S. PATENT DOCUMENTS

| | | | |
|---|---|---|---|
| 2,744,148 | 5/1956 | Ruh et al. | 260/653 |
| 3,258,500 | 6/1966 | Swamer et al. | 260/653.4 |
| 3,862,995 | 1/1975 | Martens et al. | 260/653.3 |
| 4,039,596 | 8/1977 | Pieters et al. | 260/653.7 |
| 4,052,468 | 10/1977 | Peterson et al. | 260/653.7 |

FOREIGN PATENT DOCUMENTS

| | | |
|---|---|---|
| 1369786 | 8/1964 | France. |
| 975498 | 11/1964 | United Kingdom. |
| 1006456 | 10/1965 | United Kingdom. |

*Primary Examiner*—C. Davis

[57] ABSTRACT

Chlorine atoms in chlorinated lower aliphatic hydrocarbons are replaced by fluorine in the vapor phase reaction of the chlorinated hydrocarbons with aqueous HF at 275° C. –425° C. in the presence of a metal fluoride catalyst, particularly where the metal is one or more of aluminum, nickel, or chromium. The fluorinated products are blowing agents, refrigerants, monomers, or intermediates for making them.

9 Claims, No Drawings

FLUORINATION OF CHLORINATED HYDROCARBONS

BACKGROUND OF THE INVENTION

The present invention relates to an improved chemical process, more particularly, to a halogen exchange reaction whereby chlorine is replaced by fluorine.

Halogenated lower aliphatic hydrocarbons in which halogen is fluorine or a combination of fluorine and chlorine have become increasingly important commercially in recent years as refrigerants, blowing agents for foamed plastics, and as monomers. These compounds are made industrially by the catalytic substitution of fluorine for other halogen, usually chlorine, with hydrogen fluoride. A number of metal fluorides and halogen fluorides have been used as catalysts in these reactions. The use of anhydrous HF in such reactions has been considered essential to practical operability. The more readily available and cheaper aqueous hydrofluoric acid would, of course, be preferred over the anhydrous material if these fluorination processes could be adapted to its use, not only for economic reasons, but, in many cases, also for added convenience in handling.

SUMMARY OF THE INVENTION

It has now been found that hydrogen fluoride will react with a chlorinated lower aliphatic hydrocarbon to produce a corresponding fluorinated hydrocarbon when these reactants are contacted in the vapor phase in the presence of steam at about 275° C.-425° C. in the presence of a metal fluoride catalyst, preferably an aluminum fluoride, a nickel fluoride, a chromium fluoride, or a mixture thereof. The relative proportions of HF and steam preferably correspond to vaporized aqueous hydrofluoric acid of about 20-75 percent concentration.

DETAILED DESCRIPTION OF THE INVENTION

The most convenient and most preferred concentration of aqueous HF for use in the present process is about that of the water azeotrope, variously reported as of about 35 percent to about 40 percent by weight HF. Best results are usually obtained when the HF is employed in a proportion of at least one mole per atom of chlorine to be replaced and higher proportions of HF can be used, for example, ten or more moles per atom of chlorine. Preferably, about 1.1-5 moles of HF are used per atom of chlorine desired to be replaced.

The fluorination process is applicable to chlorinated lower aliphatic hydrocarbons, that is, compounds of one to about four carbon atoms, both saturated and olefinic, and containing one or more chlorine atoms. For example, this process can be used to convert $CH_2Cl_2$ to $CH_2ClF$ and $CH_2F_2$, $CH_2ClCH_2Cl$ to $CH_2ClCH_2F$ plus $CH_2=CHF$ and $CH_3CHF_2$, vinyl chloride to vinyl fluoride, vinylidene chloride to vinylidene fluoride, propylene chloride to propylene chlorofluoride, butyl chloride to butyl fluoride, and the like. When there is more than one chlorine atom in the chlorinated hydrocarbon reactant molecule, the degree of chlorine replacement by fluorine can be controlled by varying the proportion of HF in the feed mixture. In this way, the yield of a chlorofluoro product or a difluoro product from a dichlororeactant can be maximized.

The extent of fluorination in some cases can also be influenced by the choice of reaction temperature since higher temperatures generally favor polyfluorination of compounds containing more than one chlorine substituent. However, temperatures in the higher part of the process range of 275° C.-425° C. also increasingly favor destructive fluorination and thermal cracking. Process temperatures in the approximate range of 300° C.-400° C. are preferred.

The exact composition of the metal fluoride catalyst is not known, but it is thought that oxyfluorides or hydroxyfluorides are often present as well as normal fluorides of polyvalent metals. The terms "a metal fluoride", "an aluminum fluoride", "a chromium fluoride", etc. are used herein and in the appended claims to include normal fluorides as well as oxyfluorides and hydroxyfluorides, any or all of which may be present in the catalysts used in the present process. Catalysts for the process can be prepared by exposing a granular metal compound or mixture of metal compounds to vaporized hydrofluoric acid under process conditions. The vapors may be diluted with nitrogen or other inert gas to moderate the reaction. A catalyst containing aluminum fluoride can be prepared by so exposing alumina or alumina coated or impregnated with a nickel or chromium compound or a mixture of such compounds. In many cases, a granular metal fluoride or mixture of metal fluorides can be used directly as the catalyst. Because of the extreme reactivity of hydrogen fluoride, some conventional materials are unsuitable as catalyst supports for the process. Alumina, silica, and silicates react with the HF. Carbon can be used but it has been found to cause some thermal cracking under process conditions. However, silica can be incorporated into a catalyst particle to increase porosity of the particle as the silica is reacted and removed as $SiF_4$ in the course of HF exposure. As noted above, alumina can be used to make an aluminum fluoride or oxyfluoride catalyst.

EXAMPLE 1

A fluorination catalyst consisting essentially of fluorides, oxyfluorides, or hydroxyfluorides of Ni, Cr, and Al was prepared by passing 1200 g of vaporized 38 percent aqueous HF at about 300° C. over granular activated alumina coated with 12 percent by weight of $Cr_2O_3$ and 6 percent of NiO. During this process, all of the alumina was converted to fluorides and oxyfluorides and the surface area and pore volume of the original alumina were greatly reduced by the reaction with HF.

A portion of 440 cc of this catalyst was loaded into a 5 cm × 25 cm Monel metal tube reactor which was used horizontally disposed within a tubular electric furnace. Aqueous HF of 38 percent concentration and chlorinated hydrocarbon feed were vaporized by pumping through a copper coil heated at 200° C. and the mixed vapors passed through a heated Monel metal tube to the reactor. Effluent product vapors were cooled by a water-cooled condenser and scrubbed by 10 percent aqueous NaOH before being sampled for gas chromatographic analysis.

A mixture of 38 percent aqueous HF and ethylene dichloride vapors in 3:1 molar ratio of HF to ethylene dichloride was passed over the above-described catalyst at a rate of 1.3 g/min at various temperatures. Analysis of the effluent product showed that the ethylene dichloride was converted to a mixture of cracking products, including vinyl chloride and acetylenic compounds, and fluorinated compounds such as ethylidene difluoride, vinyl fluoride, and 1-chloro-2-fluoroethane. At 415° C., 61.2 percent of the ethylene dichloride was converted, 68.5 percent of this to cracking products and the remainder to fluorinated compounds. Of the latter, ethylidene difluoride made up 41.9 mole percent, vinyl fluoride 34.3 percent, and 1-chloro-2-fluoroethane was 23.8 percent. The percent conversion to total fluorinated compounds at different reactor temperatures was as follows:

| Temp., °C.   | 250 | 300 | 350  | 415  |
|--------------|-----|-----|------|------|
| % Conversion | 2   | 3   | 10.5 | 13.5 |

EXAMPLE 2

Using the apparatus and catalyst described in Example 1, the same ratio of aqueous 38 percent HF and vinylidene chloride passed at the same rate produced a lower conversion to fluorinated products. At 420° C., 3.1 percent of the vinylidene chloride was converted to fluorinated compounds while the total conversion was 16.3 percent. Of the fluorinated products, 54.1 mole percent was 1,1,1-trifluoroethane, 21 percent was 1-chloro-1-fluoroethylene and 20.4 percent was vinylidene fluoride.

EXAMPLE 3

As in Examples 1 and 2, a 3:1 molar ratio of aqueous 38 percent HF and vinyl chloride was passed over the catalyst at 310° C. reactor temperature and at various rates. Results are listed in Table 1.

TABLE 1

| Residence time, sec. | Conversion of Vinyl Chloride | | | |
|---|---|---|---|---|
| | Total | $CH_2=CHF$ | $CH_3CHF_2$ | $C\equiv C$ |
| 4  | 5.0  | 3.0  | 2.0 | 0   |
| 6  | 6.0  | 4.0  | 2.0 | 0   |
| 10 | 9.7  | 6.5  | 2.6 | 0.5 |
| 31 | 16.6 | 11.9 | 4.7 | 1.4 |

EXAMPLE 4

The apparatus was similar to that of Example 1 except that the reactor was of brass and had a volume of 708 cc. The catalyst was also similar but was made by passing vaporized aqueous 38 percent HF at 290° C. over 6.0 percent $Cr_2O_3$, 1.5 percent NiO, and 6.0 percent $SiO_2$ on alumina until the silica had been essentially removed as $SiF_4$. The silica removal produced a more porous catalyst with greater surface area than otherwise obtained.

Mixtures of vaporized ethylene dichloride and aqueous 38 percent HF in different molar proportions were passed through the 700 cc catalyst bed at 343° C. with a residence time of about five seconds. The total conversion of ethylene dichloride to cracking products plus fluorinated compounds held fairly constant at 40–50 percent under these conditions. The conversions to fluorinated compounds, mostly vinyl fluoride, ethylidene difluoride, and ethylene chlorofluoride, are listed in Table 2.

TABLE 2

| HF/EDC (molar) | 2.0 | 8.0 | 10.0 | 12.0 | 19.5 |
|---|---|---|---|---|---|
| % Conversion to F compounds | 4.0 | 8.8 | 9.9 | 9.8 | 12.1 |

EXAMPLE 5

Using the apparatus and catalyst of Example 4, a mixture of vaporized vinyl chloride and 38 percent aqueous HF in 3:1 molar ratio of HF to vinyl chloride was passed through the reactor at 310° C. at different rates as shown in Table 3. Conversion of vinyl chloride to all products ranged from 40 percent to 50 percent while conversion to fluorinated compounds ranged from 5.4 percent to 13.8 percent. Vinyl fluoride was the major fluorinated product and 1,1-difluoroethane was the only other fluorinated hydrocarbon produced in significant quantity.

TABLE 3

| Residence time, sec. | % Conversion, Vinyl Chloride | |
|---|---|---|
| | to F Compounds | to $CH_2=CHF$ |
| 27 | 5.4  | 3.7 |
| 31 | 8.5  | 4.8 |
| 34 | 9.0  | 4.7 |
| 43 | 8.8  | 5.5 |
| 47 | 10.8 | 6.5 |
| 51 | 12.2 | 7.7 |
| 93 | 13.8 | 8.5 |

EXAMPLE 6

An apparatus similar to those of the foregoing examples was set up using Monel metal tubing and pipe throughout. The reactor was a 35.5 cm length of 1.35 cm I.D. pipe with a 0.32 cm thermocouple well running lengthwise through its center for reactor temperature measurement and control.

A Cr-Al fluoride catalyst was prepared by impregnating 45 g of 8–14 mesh alumina with an aqueous solution of 8.4 g $CrCl_3 \cdot 6H_2O$, drying the impregnated material, loading it into the above reactor to form a 28 cm bed, and passing vaporized 38 percent aqueous HF plus 50 ml/min nitrogen through the bed at 350° C. for 30 minutes, a total of 50 ml 38 percent HF being used. The nitrogen flow was continued for about 30 minutes at the same temperature after the HF flow had been stopped.

Vaporized 38 percent aqueous HF and $CH_2CL_2$ in a molar ratio of 1.4 to 1 HF to $CH_2Cl_2$ plus 51 ml/min nitrogen were passed through the catalyst bed at different temperatures and residence times to obtain the results listed in Table 4. Run times were 1.5–2 hours at each set of conditions.

TABLE 4

| Temp. °C. | Res. Time, sec. | % Conv. $CH_2Cl_2$ | % Yield | | |
|---|---|---|---|---|---|
| | | | $CH_2ClF$ | $CH_2F_2$ | $CH_3Cl$ |
| 300 | 6.6 | 9  | 29 | 31 | 40 |
| 350 | 3.5 | 12 | 2  | 73 | 24 |
| 350 | 6.1 | 13 | 16 | 44 | 39 |
| 350 | 7.7 | 14 | 37 | 34 | 29 |
| 400 | 8.8 | 30 | 11 | 47 | 24 |

The material balance was 100 percent in runs made at 300° C. and 350° C. At 400° C., the balance was 95 percent and there was an 18 percent yield of cracking products other than $CH_3CL$.

EXAMPLE 7

A chromium fluoride catalyst supported on carbon was prepared by impregnating 53.1 g of 12–20 mesh activated charcoal with an aqueous solution of 33.9 g $CrCl_3 \cdot 6H_2O$ and proceeding as in Example 6. Using the same aqueous HF—$CH_2Cl_2$ feed as in that example, results were obtained as listed in Table 5.

TABLE 5

| Temp. °C. | Res. Time, Sec. | % Conv. $CH_2Cl_2$ | % Yield $CH_2ClF$ | $CH_2F_2$ | $CH_3Cl$ |
|---|---|---|---|---|---|
| 350 | 3.5 | 68 | 20 | 58 | 7 |
| 350 | 6.1 | 42 | 36 | 45 | 18 |
| 350 | 7.7 | 71 | 6 | 20 | 5 |

The balance of the yield in each case was of other cracking products. The material balance at 7.7 seconds was 51 percent whereas at 3.5 and 6.1 seconds, material balances of 90 percent and 100 percent respectively were obtained. Carbon deposition on the catalyst was the apparent cause of gradual catalyst deactivation in the course of these experiments.

EXAMPLE 8

A nickel fluoride on carbon catalyst was prepared by the method of Example 7 by impregnating 53.8 g of 12-20 mesh activated charcoal with an aqueous solution of 15.1 g $NiCl_2 \cdot 6H_2O$ and contacting the dried material with HF as in Example 6. The resulting catalyst was contacted with vaporized 38 percent aqueous HF and $CH_2Cl_2$ in a molar ratio of 1.4:1 HF to $CH_2Cl_2$ at 350° C. as described in Example 6.

TABLE 6

| Res. Time, Sec. | % Conv. $CH_2Cl_2$ | % Yield $CH_2ClF$ | $CH_2F_2$ | $CH_3Cl$ |
|---|---|---|---|---|
| 3.5 | 62 | 18 | 11 | 9 |
| 6.1 | 29 | 44 | 27 | 17 |
| 7.7 | 34 | 29 | 22 | 9 |

Material balances for these three runs were 62 percent, 97 percent, and 86 percent, respectively.

Results similar to those listed in Examples 7 and 8 were obtained when the same $CH_2Cl_2$-38 percent HF feed was passed at essentially the same conditions over carbon-supported metal fluoride catalysts when the metal fluoride catalysts were prepared as shown from $AgNO_3$, $Co(NO_3)_2$, $La(NO_3)_3$, $SnCl_2$, $HgNO_3$, $Hg(NO_3)_2$, $CuCl_2$, $FeCl_3$, $RuCl_3$, $ZnCl_2$, NaCl, and $CaCl_2$.

Runs made as in Examples 7-8 using activated charcoal alone in the reactor produced some fluorinated products but the major products were products of thermal cracking.

We claim:

1. A process for making a fluorinated lower aliphatic hydrocarbon which comprises contacting a corresponding lower aliphatic chlorinated hydrocarbon in the vapor phase with HF in the presence of steam at about 275° C.-425° C. in the presence of a metal fluoride catalyst.

2. The process of claim 1 wherein the metal fluoride is an aluminum fluoride, a chromium fluoride, a nickel fluoride, or a mixture thereof.

3. The process of claim 2 wherein the HF and steam together are equivalent to vaporized aqueous HF of about 20-75 percent HF concentration.

4. The process of claim 3 wherein the HF is in molar excess over the chlorine to be replaced by fluorine in the chlorinated hydrocarbon.

5. The process of claim 3 wherein the HF and steam together constitute aqueous hydrofluoric acid of about 35-40 percent concentration.

6. The process of claim 3 wherein the chlorinated hydrocarbon is vinyl chloride and the fluorinated product comprises vinyl fluoride.

7. The process of claim 3 wherein the chlorinated hydrocarbon is ethylene dichloride and the fluorinated product comprises ethylene chlorofluoride, ethylidene difluoride, and vinyl fluoride.

8. The process of claim 3 wherein the chlorinated hydrocarbon is vinylidene chloride and the fluorinated product comprises vinylidene fluoride, vinylidene chlorofluoride, and 1,1,1-trifluoroethane.

9. The process of claim 3 wherein the chlorinated hydrocarbon is methylene chloride and the fluorinated product comprises methylene chlorofluoride and methylene fluoride.

* * * * *